United States Patent [19]

Steel

[11] Patent Number: 5,037,882

[45] Date of Patent: * Aug. 6, 1991

[54] SYNTHESIS OF OLIGONUCLEOTIDE ANALOGS

[76] Inventor: Samuel L. Steel, 3817 Davis Pl., Washington, D.C. 20007

[*] Notice: The portion of the term of this patent subsequent to Dec. 27, 2005 has been disclaimed.

[21] Appl. No.: 289,184

[22] Filed: Dec. 23, 1988

Related U.S. Application Data

[63] Continuation-in-part of Ser. No. 24,602, Mar. 11, 1987, Pat. No. 4,794,150.

[51] Int. Cl.$^5$ .................. C08F 283/00; C08G 63/48; C08G 63/91
[52] U.S. Cl. .................. 525/54.11; 530/333; 530/334; 422/131; 422/134
[58] Field of Search .................. 422/131, 134; 525/54.11; 530/333, 334

[56] References Cited

U.S. PATENT DOCUMENTS

| | | | |
|---|---|---|---|
| 3,814,732 | 6/1974 | Wang | 525/54.11 |
| 4,517,338 | 5/1985 | Urdea et al. | 525/54.11 |
| 4,638,032 | 1/1987 | Benner | 525/54.11 |

*Primary Examiner*—Nathan M. Nutter
*Attorney, Agent, or Firm*—Edwin D. Schindler

[57] ABSTRACT

A novel polymeric support is provided for carrying out the synthesis of oligonucleotide analogs via solid-phase synthesis techniques. The suitably-shaped polymeric disc, wafer, etc., of the invention may be made of polystyrene, silica gel, glass beads, polyamide/kieselguhr, cellulose, etc. The suitably-shaped disc or wafer of the invention should, preferably, have a thickness of 200–400 μm and may be of any suitable length or width. A process for the synthesis of oligonucleotide analogs utilizing the polymeric support of the present invention is also disclosed.

23 Claims, 1 Drawing Sheet

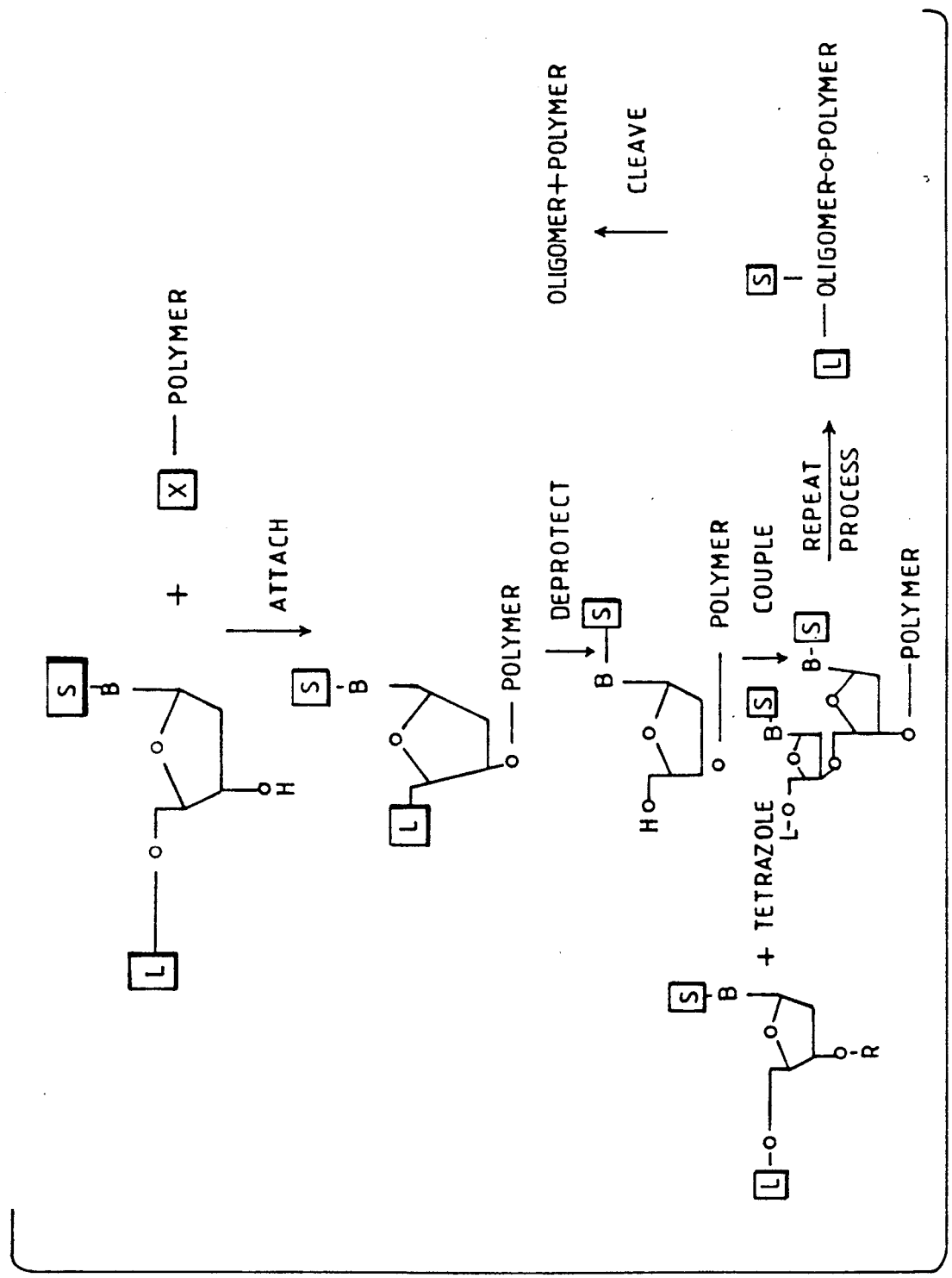

SYNTHESIS OF OLIGONUCLEOTIDE ANALOGS

CROSS-REFERENCE TO RELATED APPLICATION

This application is a continuation-in-part of application Ser. No. 07/024,602, filed Mar. 11, 1987 and now U.S. Pat. No. 4,794,150.

BACKGROUND OF THE INVENTION

1. Technical Field of the Invention

The present invention relates to the synthesis of oligonucleotide analogs. More particularly, the invention relates to a novel polymeric disc, wafer or other similarly shaped resin (e.g., planar and non-planar) and a method for its use in solid-phase synthesis.

The present invention permits the rapid production of oligonucleotide analogs, i.e., numerous oligonucleotides differing from one another by only a single base or a small number of bases. The synthesis of analogs according to the present invention can take place at a rapid rate while assuring that the reagents necessary to synthesize the analogs undergo quantitatively complete reactions so as to minimize undesirable side-reaction products which could result in the production of "deletion peptides" or "deletion sequences."

Within recent years, oligonucleotides have been used in crystallographis and biochemical studies of DNA and RNA sequencing and as site-specific mutagens. This and related activity has created an increased need for the chemical synthesis of oligonucleotides and small genes. The present invention greatly simplifies and increases the efficiency of the task of preparing synthetic oligonucleotides.

2. Description of the Prior Art

In the field of peptide chemistry, solid phase peptide synthesis ("SPPS") was introduced by Dr. R. Bruce Merrifield in 1963 when Dr. Merrifield attached a growing peptide chain to a solid support. Merrifield, R. B. (1963) *J. Am. Chem. Soc.* 85, 2149-2154. The procedures enunciated by Dr. Merrifield for SPPS were as follows: An amino acid corresponding to the C-terminal of the target peptide is covalently attached to an insoluble polymeric support ("the resin"). The next amino acid, with a protected α-amino acid, is activated and reacted with the resin-bound amino acid to yield an amino-protected dipeptide on the resin. Excess reactants and co-products are removed by filtration and washing. The amino-protecting group is removed by and chain extension is continued with the third and subsequent protected amino acids. After the target protected peptide chain has been built up in this stepwise fashion, all side chain groups are removed and the anchoring bond between the peptide and the resin is cleaved by suitable chemical means thereby releasing the crude peptide product into solution. The desired peptide then undergoes an extensive purification procedure and is then characterized. Kent, S. & Clark-Lewis, I., "Modern Methods for the Chemical Synthesis of Biologically Active Peptides," Division of Biology 147-75, California Institute of Technology, Pasadena, Calif. 91125 U.S.A.; Houghten, R. A., Chang, W. C. & Li, C. H. (1980), *Int. J. Pept. Protein Res.*, 16, 311-320; Houghten, R A., Ostresh, J. M. & Klipstein, F. A. (1984), *Eur. J. Biochem.*, 145, 157-162; Stewart, J. M. & Young, J. D., *Solid Phase Peptide Synthesis*, Pierce Chemical Company (2d ed. 1984). See, also, Geysen, H. M., 20 Meloen, R. H. & Baretling, S. J. (1984) *Proc. Natl. Acad. Sci. USA*, 81, 3998-4002; Matthes, H. W. D., Zenke, W. M., Grundstrom, T. Staub, A., Wintzerith, M. & Chambon P., (1984) *The EMBO Journal*, 3, 801-805.

The resin employed in standard SPPS is known as the "Merrifield resin" and is a polystyrene bead of 100-200 microns in size. The resin typically contains 0.5-2.0% divinylbenzene cross-linkage and contains 0.2 to 0.8 mmole of p-chloromethyl groups per gram resin. The number of p-chloromethyl groups determines the number of individual chains per gram and their ultimate size. The size of the bead allows for a rapid penetration of reagents in SPPS. The percentage of cross-linkage determines the extent to which the resin shrinks and swells during solvent changes. A large shrink-and-swell effect is preferred.

In the field of oligonucleotide chemistry, on the other hand, Dr. Khorana has developed techniques, which were used by others in solution-phase synthesis, for solid-phase synthesis. In doing so, Dr. Khorana eliminated the intensive purification procedures required between each chemical step; the solid-phase procedure only required filtration and rinsing of the solid support with fresh solvent. Solid-phase synthesis permitted chemists to add 15-16 nucleotides per day rather than four or five nucleotides per week.

While the solid phase techniques had revolutionized biomedical research in industry and academia, this procedure has remained essentially unchanged since its inception in the early 1960's. With the explosive pace at which biotechnical research has been advancing in the industrialized nations of the world, substantially more oligonucleotides, particularly analogs, of greater complexity are needed in industry and research than ever before. The ever increasing demand for analog oligonucleotides has been approached in several ways, but no approach thus far, has proven completely satisfactory.

SUMMARY OF THE INVENTION

In accordance with the present invention, provided is a novel polymeric disc, wafer or similarly shaped resin for carrying out the synthesis of oligonucleotide analogs via the solid-phase synthesis techniques generally known and described above. The polymeric disc of the present invention may be made out of, for example, five supports presently used in DNA synthesis: polystyrene, silica gel, glass beads, polyamide/kieselguhr and cellulose (e.g., cellulose paper.) If the disc is made of cross-linked polystyrene, preferably there would be 2-5% cross-linkage.

The inventive polymeric disc, which it will be understood as including all suitably shaped and sized resins, whether planar or non-planar, spherical, etc., not merely that which may be thought of as a circular disc, should be sufficiently thin so as to allow for the rapid penetration of reagents to insure that the required reactions may run to completion. The disc of the invention should, preferably, have a thickness of 200-400 μm. Aside from this parameter, i.e., the thickness of the disc, the precise shape of the disc, it should be emphasized, may be any shape having any suitable length or width whatsoever depending upon the requirements of the user.

As part of the present invention, a process for the synthesis of oligonucleotide analogs, using the polymeric resin disc of the invention is further disclosed.

BRIEF DESCRIPTION OF THE DRAWINGS

In the Drawing:

The FIGURE outlines the experimental process of solid-phase oligonucleotide synthesis.

DETAILED DESCRIPTION OF THE PREFERRED EMBODIMENTS

The concept of solid-phase peptide synthesis and, as will be explained, as it relates to the present invention may best be understood by reference to the experimental procedure outlined in the FIGURE, wherein X is a reactive group, such as an alkylamine group; L is a labile protecting group; and S is a stable side-chain blocking group to prevent side chain reactions during the oligonucleotide synthesis.

Referring to the FIGURE, a synthetic polymer, such as the polymeric disc of the present invention, would bear reactive groups, X. The nucleotide which will form the 3'-terminal residue of the oligonucleotide to be synthesized is converted to a derivative in which its 5'-hydroxyl group is protected by a labile protecting group, L. Any standard protecting group, such as, for example, the dimethoxytrityl group, may be used in conjunction with the present invention. The foregoing derivative of the 3'-terminal nucleotide is coupled to the reactive polymer. At this point, the repetitive cyclic part of solid-phase synthesis begins. A reagent is applied to the protected polymer to remove the labile blocking group, L, from the nucleotide residue. The reagent employed must not, in any way, harm the link of the 3'-terminal residue to the polymer. Moreover, if the nucleotide attached to the polymer (and all nucleotides in the oligomer to be synthesized) contains a side-chain reactive functional group, that functional group must be blocked by a stable blocking group, S, which will remain completely intact throughout the synthesis, but which can be removed finally to yield the free oligonucleotide. Following removal of the labile protecting group, the next nucleotide is coupled to the polymer by use of a suitable coupling reaction. Again, the 5'-hydroxyl must be protected with the labile group.

This cycle of deprotection and coupling is then repeated with each nucleotide which is to be incorporated into the nucleotide chain. For the deprotection reaction, standard acidolysis methods, such as, a 3% solution of dichloroacetic acid in dichloromethane may be used. Tetrazole may be employed as the activating agent, as well as other suitable agents for use with the present invention. Finally, after the entire blocked oligomer has been assembled on the polymer support, such as the present invention, a different type of reagent, e.g., ammonium hydroxide, is applied to cleave the oligomer from the polymer and allow it to be dissolved. The blocking groups, which have protected side-chain functional groups, must also be removed, and are usually chosen so that they can be removed simultaneously with the cleavage of the oligomer from the resin.

The present invention concerns the polymer support to be employed in the foregoing solid-phase synthesis framework. The support must be insoluble and have satisfactory means of attaching the first nucleotide to it. The polymeric disc of the present invention, i.e., the polymer support, may be made out of those resin materials presently used for solid-phase synthesis when such is carried out with fine bead resins via conventional means. The polymeric disc, which may have any desired shape suitable for the user (e.g., any suitable length or width; planar or non-planar) should, preferably, have a thickness of 200-400 $\mu$m. The resin of the present invention may be made out of, for example, polystyrene, silica gel, glass beads, polyamide/kieselguhr and cellulose. If cross-linked polystyrene is to be the material of the resin, the composition of the resin should be at least 1% divinylbenzene; a resin with substantially less than 1% divinylbenzene would be too fragile to be of any use to the chemist.

Additionally, the inventive resin, to be effective, need not rely upon permeation, but may effectively act via a surface reaction. Thus, a hybrid resin may have a strong, inert support, or backing, made of, for example, plastics or nylons (e.g., Nylon-66), or other materials.

The present invention further includes a method for use of the novel polymeric disc. In the synthesis of analogs, discs would be individually tagged. Oligonucleotide synthesis upon the severally tagged discs would take place within one reaction vessel in accordance with known principles of solid-phase synthesis. When the point of deviation in the oligomers is reached, i.e., where the nucleotide(s) which are to differ from one oligonucleotide analog to another in the synthesis process is reached, the discs of the invention can be separated by hand or other procedure (e.g., tongs), reacted separately in different reaction vessels and then, subsequently, again placed in the same reaction vessel to continue or complete the synthesis of the analog chain with those nucleotides generally common to the oligonucleotides.

Finally, a hybrid-type resin, having an inert support as described above, which relies upon a surface reaction, can also be conveniently transferred between reaction vessels with conventional tongs.

The invention will now be more fully described by reference to the following Example. It should, however, be understood that the following Example is for purposes of illustration only and not meant for the purpose of defining the limits or scope of the invention.

EXAMPLE

The following procedure is suggested for the synthesis of the following three oligonucleotide analogs:

$$\xrightarrow{\text{direction of synthesis}}$$
1) A—C—C—G—T
2) A—I—C—G—T
3) A—C—C—I—T wherein,
A = adenine;
C = cytosine;
I = inosine;
G = guanine; and
T = thyymine.

Step 1: Place 3 discs into a reaction vessel.
Step 2: Rinse discs as follows:
  2×20 ml acetonitrile; and,
  2×20 ml dichloromethane.
Step 3: Derivatize the discs using succinylated 5'-O-dimethoxytrityladenosine in dioxane, pyridine, p-nitrophenol and dicyclohexylcarbodiimide, and let stand overnight.
Step 4: Wash discs extensively with:
  2×20 ml, N,N dimethylformamide;
  2×20 ml methanol; and,
  2×20 ml ether.

Step 5: Deprotect with 20 ml 3% dichloroacetic acid in dichloromethane for 2×20 seconds, then rinse two times with the same solution for 5 seconds each.

Step 6: Wash with 5×20 ml dichloromethane.

Step 7: Remove Disc #2 and place in second reaction vessel.

Step 8: Dry both vessels under argon gas.

Step 9: Add 1:1 of 0.5M tetrazole and 0.2M 5'-O-dimethoxytritylcytosine-phosphoramidite to Reaction Vessel #1 in a 20-fold excess for the nucleotide. Thereafter, add (1:1) 0.5M tetrazole and 0.2M 5'-O-dimethoxytritylinosine-phosphoramidite to Reaction Vessel #2 in 20-fold for the nucleotide and then react the contents of both reaction vessels (i.e., Reaction Vessels #1 and #2) for 3 minutes.

Step 10: Wash Reaction Vessels #1 and #2 with 20 ml acetonitrile.

Step 11: Re-place Disc #2 into Reaction Vessel #1 and oxidize with 0.1M $I_2$ solution in approximately 10-20 ml of tetrahydrofuran (THF).

Step 12: Wash with:
2×20 ml acetonitrile; and,
2×20 ml dichloromethane.

Step 13: Repeat Step Nos. 5, 6 and 8.

Step 14: Add in a 1:1 ratio, 0.5M tetrazole and 0.2M 5'-O-dimethoxytritylcytosine-phosphoramidite in an excess of approximately 20-fold.

Step 15: Repeat Steps Nos. 10-12 and 5-6.

Step 16: Remove Disc #3 and place in Reaction Vessel #2.

Step 17: Repeat Step No. 8.

Step 18: Add in a 1:1 ratio, 0.2M of 5'-O-dimethoxytritylguanosine-phosphoramidite to Reaction Vessel #1 in an approximately 20-fold excess. Thereafter, add in a 1:1 ratio, 0.5M tetrazole and 0.2M of 5'-O-dimethoxytritylinosinephosphoramidite to Reaction Vessel #2 in an excess of approximately 20-fold and then react the contents of both reaction vessels for 3 minutes.

Step 19: Repeat Steps Nos. 10-13.

Step 20: Add in a 1:1 ratio 0.5M tetrazole and 0.2M of 5'-O-dimethoxytritylthymosinephosphoramidite to Reaction Vessel No. 1 in an excess of approximately 20-fold and then react the contents of the vessel for 3 minutes.

Step 21: Repeat Steps Nos. 10-13.

Step 22: Cleave oligomers off discs in separate vessels, overnight, using warm ammonium hydroxide.

Step 23: Lyophilize the ammonium hydroxide solution to recover crude oligomers.

While only several embodiments of the present invention have been shown and described, it will be obvious to those skilled in the art that many modifications may be made thereunto without departing from the spirit and scope of the invention.

What is claimed is:

1. Apparatus for a solid-phase synthesis of oligonucleotide analogs, comprising:
a polymeric support being insoluble and capable of permitting an attachment to it of a first nucleotide in said solid-phase synthesis, said polymeric support including an inert support which is capable of permitting a transfer of said polymeric support from a first reaction vessel to a second reaction vessel by means of a tongs instrument; and,
reactor cell means for use in combination with said polymeric support, said reactor cell means including a plurality of reaction vessels wherein at least one of said reaction vessels of said reactor cell means is capable of at least partially containing a plurality of said polymeric supports during said solid-phase synthesis, said polymeric support being suitably shaped and sized for use in combination with said reactor cell means.

2. Apparatus for a solid phase synthesis according to claim 1, wherein said polymeric support is made of a member selected from the group consisting of polystyrene, silica gel, glass beads, polyamide/kieselguhr, cellulose and a combination thereof.

3. Apparatus for a solid phase synthesis according to claim 2, wherein said polymeric support is cellulose paper.

4. Apparatus for a solid phase synthesis according to claim 1, wherein said inert support is a nylon.

5. Apparatus for a solid phase synthesis according to claim 1, wherein said inert support is glass.

6. Apparatus for a solid phase synthesis according to claim 1, wherein said polymeric support is planar.

7. Apparatus for a solid phase synthesis according to claim 1, wherein said polymeric support is non-planar.

8. Apparatus for a solid phase synthesis according to claim 1, wherein said polymeric support has an average thickness of 200-400 μm.

9. A process for the synthesis of oligonucleotide analogs, comprising the steps of:
(a) tagging a set of separate and suitably shaped and sized polymeric supports for use in a solid-phase synthesis of said oligonucleotide analogs so that each of said separate polymeric supports is designated for the synthesis of one or more of said oligonucleotide analogs;
(b) placing said separate polymeric supports into at least one reaction vessel having reagents for the solid phase synthesis of a nucleotide sequence of said oligonucleotide analogs wherein said nucleotide sequence of said oligonucleotide analogs is to be common to said oligonucleotide analogs being synthesized; and,
(c) placing said separate polymeric supports into separate reaction vessels having reagents for said solid phase synthesis of nucleotide sequences of said oligonucleotide analogs which are not to be common to all of said oligonucleotide analogs being synthesized, wherein at least one of said placing steps is carried out with a tongs instrument.

10. The process according to claim 9, wherein said step (b) is carried out with one reaction vessel.

11. The process according to claim 9, wherein the number of said reaction vessels employed in step (c) is at least one greater than the number of said reaction vessels employed in step (b).

12. The process according to claim 9, wherein said separate reaction vessels are capable of being a single reaction vessel at differing points in time.

13. The process according to claim 9, wherein said separate polymeric resins are made of a member selected from the group consisting of polystyrene, silica gel, glass beads, polyamide/kieselguhr, cellulose and a combination thereof.

14. The process according to claim 9, wherein said separate polymeric supports include an inert support.

15. The process according to claim 9, wherein said inert support is glass.

16. The process according to claim 9, wherein said separate polymeric supports include an inert support which is capable of permitting a transfer of said separate polymeric supports from a first reaction vessel to a second reaction vessel by means of a tongs instrument.

17. A process for the synthesis of oligonucleotide analogs, comprising the steps of:
(a) tagging a set of separate and suitably shaped and sized polymeric supports for use in a solid-phase synthesis of said oligonucleotide analogs so that each of said separate polymeric supports is designated for the synthesis of one or more of said oligonucleotide analogs, said polymeric supports including an inert support which is capable of permitting a transfer of said polymeric supports from a first reaction vessel to a second reaction vessel by means of a tongs instrument;
(b) placing said separate polymeric supports into at least one reaction vessel having reagents for the solid phase synthesis of a nucleotide sequence of said oligonucleotide analogs wherein said nucleotide sequence of said oligonucleotide analogs is to be common to said oligonucleotide analogs being synthesized; and
(c) placing said separate polymeric supports into separate reaction vessels having reagents for said solid phase synthesis of nucleotide sequences of said oligonucleotide analogs which are not to be common to all of said oligonucleotide analogs being synthesized.

18. The process according to claim 17, wherein at least one of said placing steps is carried out with a tongs instrument.

19. The process according to claim 17, wherein said step (b) is carried out with one reaction vessel.

20. The process according to claim 17, wherein the number of said reaction vessels employed in step (c) is at least one greater than the number of said reaction vessels employed in step (b).

21. The process according to claim 17, wherein said separate reaction vessels are capable of being a single reaction vessel at differing points in time.

22. The process according to claim 17, wherein said separate polymeric resins are made of a member selected from the group consisting of polystyrene, silica gel, glass beads, polyamide/kieselguhr, cellulose and a combination thereof.

23. The process according to claim 17, wherein said inert support is glass.

* * * * *